(12) United States Patent
Yue

(10) Patent No.: US 10,342,725 B2
(45) Date of Patent: Jul. 9, 2019

(54) SYSTEM AND METHOD FOR USER-CONTROLLED EXOSKELETON GAIT CONTROL

(71) Applicant: Kessler Foundation Inc., West Orange, NJ (US)

(72) Inventor: Guang Yue, West Caldwell, NJ (US)

(73) Assignee: Kessler Foundation Inc., West Orange, NJ (US)

( * ) Notice: Subject to any disclaimer, the term of this patent is extended or adjusted under 35 U.S.C. 154(b) by 1081 days.

(21) Appl. No.: 14/679,419

(22) Filed: Apr. 6, 2015

(65) Prior Publication Data

US 2016/0287463 A1    Oct. 6, 2016

(51) Int. Cl.
| A61H 3/02 | (2006.01) |
| A61H 3/00 | (2006.01) |
| A61F 2/68 | (2006.01) |
| A61H 1/02 | (2006.01) |

(52) U.S. Cl.
CPC ............... *A61H 3/00* (2013.01); *A61F 2/68* (2013.01); *A61H 1/0244* (2013.01); *A61H 3/02* (2013.01); *A61H 2003/007* (2013.01); *A61H 2201/0173* (2013.01); *A61H 2201/165* (2013.01); *A61H 2201/5023* (2013.01); *A61H 2201/5061* (2013.01); *A61H 2201/5097* (2013.01)

(58) Field of Classification Search
CPC ...................... A61H 3/00; A61H 1/0237–0262
See application file for complete search history.

(56) References Cited

U.S. PATENT DOCUMENTS

| 7,153,242 B2 | 12/2006 | Goffer |
| 7,190,141 B1 | 3/2007 | Ashrafiuon et al. |
| 7,346,396 B2 | 3/2008 | Barriskill et al. |
| 8,096,965 B2 | 1/2012 | Goffer et al. |
| 8,231,688 B2 | 7/2012 | Fairbanks et al. |
| 8,348,875 B2 | 1/2013 | Goffer et al. |
| 8,419,804 B2 | 4/2013 | Herr et al. |
| 2007/0123997 A1 | 5/2007 | Herr et al. |
| 2011/0105966 A1 | 5/2011 | Kazerooni et al. |
| 2011/0166489 A1 | 7/2011 | Angold et al. |
| 2012/0004736 A1 | 1/2012 | Goldfarb et al. |
| 2012/0101415 A1 | 4/2012 | Goffer et al. |
| 2012/0172770 A1 | 7/2012 | Almesfer et al. |
| 2013/0158445 A1* | 6/2013 | Kazerooni .............. A61H 3/00 601/35 |
| 2013/0231595 A1* | 9/2013 | Zoss .................... A61H 1/0255 601/34 |
| 2013/0237884 A1* | 9/2013 | Kazerooni .............. A61H 3/00 601/34 |

(Continued)

OTHER PUBLICATIONS

Higuchi, Masaru et al, Development of a Walking Assist Machine Using Crutches (Composition and Basic Experiments), Journal of MEchanical Science and Technology 24 (2010) 245-48.*

(Continued)

*Primary Examiner* — Timothy A Stanis

(57) ABSTRACT

A wearable robotic exoskeleton system and method is provided to offer mobility to a user wherein the exoskeleton system implements at least a safety state and an operational state, and wherein when in the operational state, the user is enabled to control the gait implemented by the exoskeleton system by varying gripping pressure applied to external supports.

19 Claims, 5 Drawing Sheets

(56) References Cited

U.S. PATENT DOCUMENTS

2014/0196757 A1* 7/2014 Goffer ................ A61H 3/02
 135/66
2014/0358290 A1* 12/2014 Kazerooni ............ G05B 15/02
 700/275
2015/0351991 A1* 12/2015 Amundson ............ A61H 3/00
 623/24

OTHER PUBLICATIONS

Hasegawa et al., "Finger-mounted walk controller of powered exoskeleton for paraplegic patient's walk," World Automation Congress (WAC), pp. 400-405, Aug. 2014.

* cited by examiner

SYSTEM AND METHOD FOR USER-CONTROLLED EXOSKELETON GAIT CONTROL

FIELD OF THE INVENTION

The instant invention generally relates to a wearable exoskeleton for use by individuals with mobility disorders, and specifically to such a system having a safety state and an operational state for user-controlled gait operation.

All documents cited to or relied upon below are expressly incorporated herein by reference.

BACKGROUND OF THE INVENTION

Advancements have occurred in recent years for robotic exoskeletons for lower extremities to restore ambulation that has been impaired or lost due to paraplegia as a result of, for example, spinal cord injury (SCI). In particular, exemplary systems have been commercialized to the extent that they are undergoing clinical trials and user evaluations including such systems from, for example, Ekso Bionics Holdings, Inc. of Richmond, Calif., ReWalk Robotics Ltd. of Yokneam Bit, Israel, and Rex Bionics Ltd. of Auckland, New Zealand.

However, current exoskeletons are software controlled to provide a preprogrammed gait for mobility with little wearer, i.e., user, control other than to initiate or stop mobility, including such systems disclosed in U.S. Pat. No. 8,348,875, U.S. Patent Appln. Publn. No. 2013/0158445 and Y. Hasegawa and K. Kakayama, "Finger-Mounted Walk Controller of Powered Exoskeleton for Paraplegic Patient's Walk," World Automation Congress Conference, Aug. 3-7, 2014. Such current systems fail to provide the user or wearer with any control of the length or amplitude and frequency of the stride, gait and overall speed of walking. Instead, current systems only provide the ability to initiate or stop the mobility provided by the preprogrammed gait. Therefore, walking with current exoskeletons is an automated process with little or no actual user control.

As a consequence, current lower extremity exoskeletons do not succeed in providing independent ambulation for disabled individuals due to their lack of user control. The expense and training required for current devices, therefore, has not been fully justified.

Moreover, current exoskeletons fail to provide adequate and convenient safety and operational states to enable mobility based upon a user-controlled gait operation where user inputs only cause mobility when such user in a position that such mobility would not cause a potential fall or harm to the user.

Accordingly, there exists a need in the art for an exoskeleton having safety and operational states and enabling a user-controlled gait operation only when such user-controlled gait operation would not cause a potential fall or harm to the user.

SUMMARY OF THE INVENTION

The present invention is directed to a wearable robotic exoskeleton system having a safety state and an operational state for user-controlled gait operation. In one exemplary embodiment, the exoskeleton system comprises first and second supports configured to be coupled to a user's lower limbs; first and second actuators respectively coupled to the first and second supports with the first and second actuators configured to provide movement of the exoskeleton; and a controller coupled to the first and second actuators, wherein the controller is configured to shift the exoskeleton between a plurality of operational states including at least a safety state and an operational state based upon receipt of user command signals. The system further comprising at least one support device separate from the exoskeleton to be held by a user for stabilization, with the support device including at least one support handle having at least one sensor coupled to the controller, wherein the sensor generates the user command signals based upon detecting one or more of finger or hand contact and/or pressure applied against the sensor, and the controller interprets the user command signals to determine one of a secure gripping condition or an insecure gipping condition.

In one such embodiment, the controller advantageously causes the exoskeleton to operate in the safety state if the gripping condition is interpreted as insecure, and the operational state if the gripping condition is interpreted as secure. In the operational state, the controller causes movement of the respective leg supports based upon receipt of user command signals indicative of the sensor detecting a predetermined contact force and/or pressure applied against the sensor.

The invention is also directed to a method of operation of a wearable robotic exoskeleton for implementing the safety state and operational state for user-controlled gait operation. In accordance with one exemplary embodiment, the exoskeleton system controller receives user command signals generated by the sensors on the support handles based upon detecting one or more of finger or hand contact and/or pressure applied against the sensor. The controller interprets the user command signals to determine one of a secure gripping condition or an insecure gripping condition, and operates the exoskeleton in a safety state if said gripping condition is interpreted as insecure. In the alternative, the controller operates the exoskeleton in an operational state if the gripping condition is interpreted as secure. In the operational state, the controller further causes movement of the respective supports based upon receipt of user command signals indicative of the sensor detecting a predetermined contact and/or pressure applied against the sensor.

The invention is further directed to a system useable with a wearable robotic exoskeleton for providing safety and operational states for user-control of the gait and mobility. In accordance with an exemplary embodiment, the system comprises a controller configured to be coupled to an exoskeleton's first and second actuators of respective first and second supports configured to be coupled to a user's lower limbs. The controller is configured to shift said exoskeleton between a plurality of operational states including at least a safety state and an operational state based upon receipt of user command signals. The system further includes at least one support device to be held by a user of the exoskeleton for stabilization. The support device includes at least one support handle having at least one sensor coupled to the controller. The sensor generates user command signals based upon detecting one or more of finger or hand contact and/or pressure applied against the sensor. The controller interprets the user command signals to determine one of a secure gripping condition or an insecure gripping condition.

The controller is configured to cause the exoskeleton to operate in the safety state if the gripping condition is interpreted as insecure; and in the operational state if the gripping condition is interpreted as secure. In the operational state, the controller is configured to cause movement of the respective supports based upon receipt of user command signals indicative of the sensor detecting a predetermined contact and/or pressure applied against the sensor.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical systems and arrangements. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The present invention generally relates to a wearable robotic exoskeleton system and method for providing advantageous user-controlled gait and mobility with a safety operational state. The invention is useful, for example, with paraplegics and for other individuals having lower extremities with limited mobility.

Exemplary Embodiments of the Invention

A wearable robotic exoskeleton system is provided to offer mobility to a user wherein the exoskeleton system implements at least a safety state and an operational state. In the operational mode, the user is enabled, for example, to control the gait implemented by the exoskeleton system. As used herein, "gait" is intended to mean the manner in which the exoskeleton moves the user's lower extremities to create movement such as walking, including, individually and in combination, the stride length of respective feet alone, the height of foot clearance above the ground during a stride (referred to herein as "HFC"), the speed or velocity of the respective lower extremity during a stride, and the number of walking strides made in a unit of time.

Figure 1:
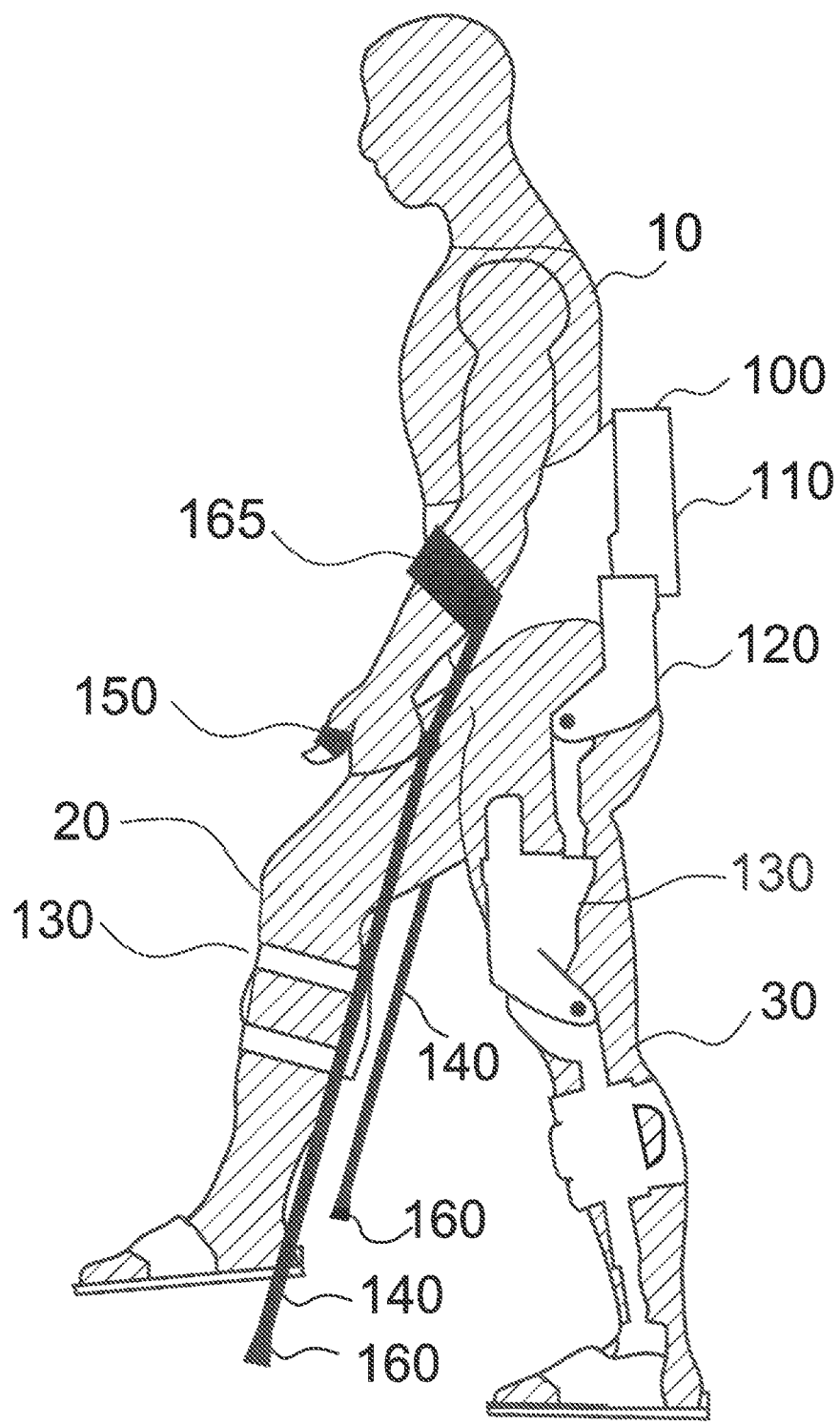
FIG. 1 is a schematic view of a user wearing a robotic exoskeleton system in accordance with an exemplary embodiment of the present invention.

FIG. 1 depicts a user 10 wearing a robotic exoskeleton system 100 in accordance with an exemplary embodiment of the present invention. The exoskeleton system 100 includes a controller 110 coupled to left and right actuators 120 (only the left actuator is shown in FIG. 1). The left and right actuators 120 are mechanically coupled to corresponding left and right leg supports 130 attachable to right and left lower extremities 20 and 30 of the user 10. The exoskeleton system 100 further includes separate support devices 140 for use in stabilizing the user 10 while the exoskeleton system 100 is in operation.

Figure 2:
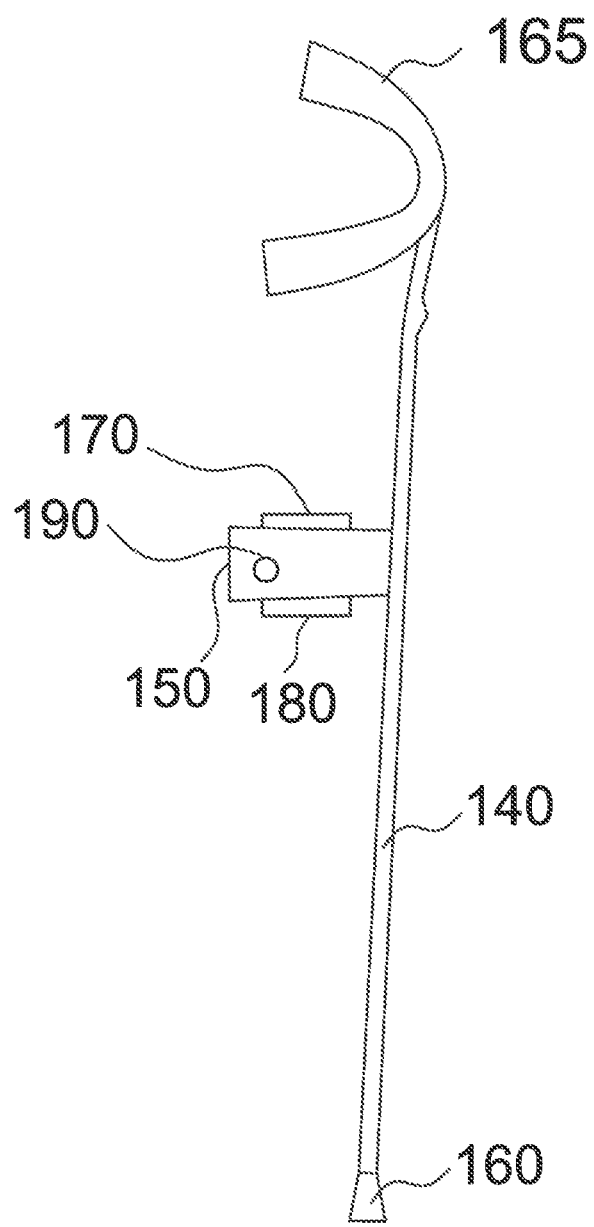
FIG. 2 is a perspective view of a separate support device of a robotic exoskeleton system in accordance with an exemplary embodiment of the present invention.

Each separate support device 140 includes a support handle 150 and a tip 160 for contact with the ground or floor. In addition, the separate support device 140 may include an arm brace 165 for securing to, for example, a fore arm as shown in FIG. 1. Greater detail of an exemplary separate support device 140 is depicted in FIG. 2.

The controller 110 may be a computer, microprocessor, microcontroller, portable computing device or other system capable of receiving signals from sensors and providing control instructions to actuators for movement of exoskeleton leg supports. In addition, many configurations of actuators, leg and other support elements, and the manner in which such supports are attached to a user may be envisioned by one skilled in the art for the exoskeleton system 100 in accordance with the invention. Any exoskeleton system that enables independent control of movement of the lower extremities may be used for the exoskeleton system 100. Suitable robotic exoskeletons for the present invention include presently available robotic exoskeletons manufactured by, for example, Ekso Bionics Holdings, Inc. of Richmond, Calif., ReWalk Robotics Ltd. of Yokneam Ilit, Israel, and Rex Bionics Ltd. of Auckland, New Zealand.

In addition, devices useable for the separate support device 140 include, for example, a crutch, cane or walker.

Also, it should be readily understood that the exoskeleton 100 depicted in FIG. 1 only includes those elements necessary for practicing the present invention for ease of explanation and other element typically required for operation of an exoskeleton system and controller to be operational are not shown including, for example, other retaining devices and braces for securing the exoskeleton system 100 to the user 10 as well as electrical power from a power supply such as a battery, rechargeable or otherwise.

In FIG. 2, the support handle 150 of the separate support device 140 includes sensors 170 and 180 to detect a gripping condition and optionally movement of fingers (not shown) of the user 10, and an optional state/mode sensor 190. The sensors 170 and 180 are coupled to the controller 110 to enable the sensors 170 and 180 to communicate user command signals to the controller 110. The optional state/mode selector sensor 190 is also coupled to the controller 110 to enable the user 10 to communicate the desired state or mode in which the exoskeleton system 100 should be operated. Suitable sensors useable for the sensor(s) 170, 180 and/or 190 of the present invention include, for example, conventional electro-mechanical sensors, capacitive- or resistance-touch sensors or pressure sensors.

The specific mechanism or arrangement chosen for the coupling that enables the communication between the sensors 170, 180 and 190, and the controller 110 are not critical to practicing the present invention and may be implemented, by for example, a wired or wireless connections or via optical fiber or other transmission mediums that enables communications between sensors and a controller. Suitable wireless communication methods for the sensors 170, 180 and 190 include, for example, standardized wireless communication methods such as specified by the Bluetooth® and Zigbee® wireless communication standards.

The location of sensor 180 detects pressure or force applied by one or a plurality of the user's fingers. The location of sensor 170 facilitates such sensor to contact the palm of the user's hand and detect when the user 10 leans or puts her/his weight on the support handle 150. The sensors 170 and 180 may also be used in combination to detect the gripping pressure applied by the user 10 on the support handle. It should be further readily understood that to the extent that an exoskeleton system does not utilize the user applying his weight or leaning on the support handle 150 to generate a corresponding user command then the sensor 170 may be omitted from the support handle 150 in accordance with the invention.

In addition, the optional state/mode selector sensor 190 may also be a slide switch, button(s) switch, dial switch or other mechanism that enables the user 10 to select the state or mode of exoskeleton operation. The state/mode selector sensor 190 is disposed at a representative location on the support handle 150 in FIG. 2 to facilitate use by the user 10 without fatigue or strain. However, it should be readily understood that such location of the state/mode selector sensor 190 is a design choice that is not critical to practicing the present invention, and it may alternately be disposed on the top or bottom of the support handle 150, or omitted all together. If omitted, the operations of the state/mode selector sensor 190 may be performed, for example by, the sensors 170 and 180, alone or in combination, as described with respect to, for example, FIG. 4. In a similar manner, either one of the sensors 170 or 180 may be omitted in accordance with the invention with the described functions performed by the other remaining sensor.

Figure 3:
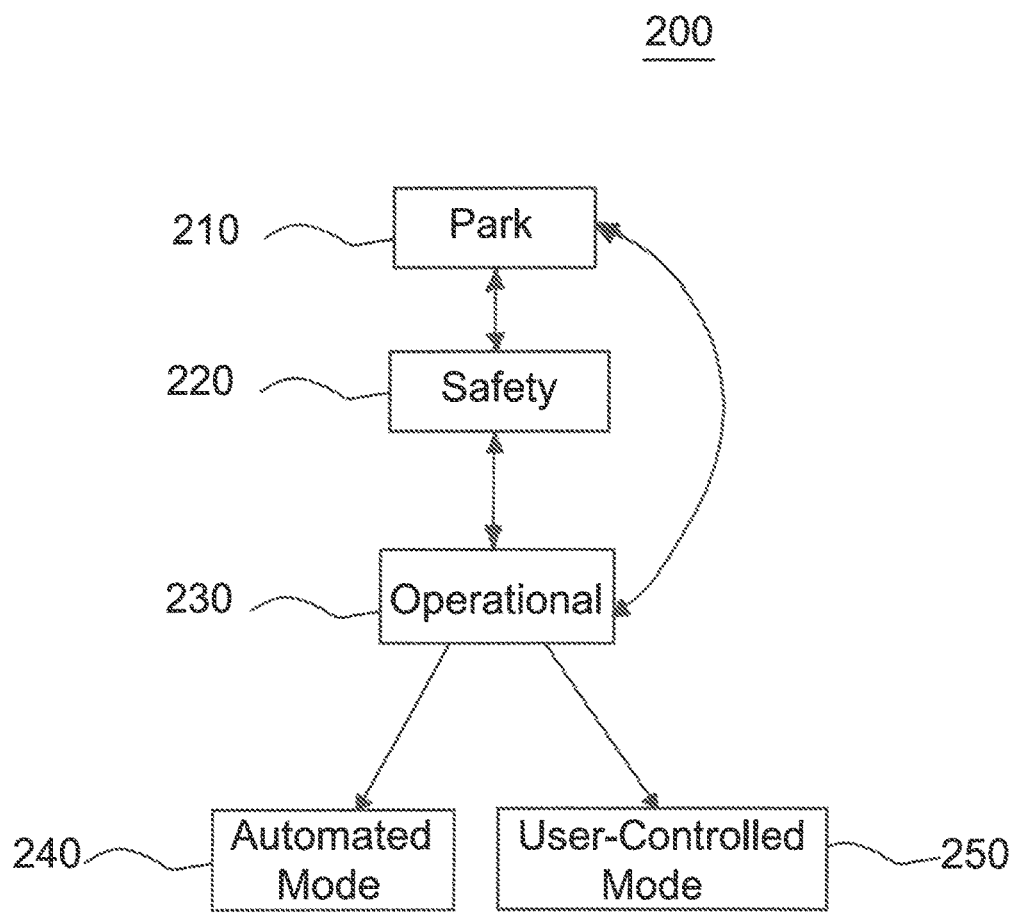
FIG. 3 is a diagram of operational states of a robotic exoskeleton system in accordance with an exemplary embodiment of the present invention.

FIG. 3 depicts exemplary operational states 200 in which the controller 110 may implement for the exoskeleton system 100 based upon the user's selection using, for example, the state/mode selector sensor 190 of FIG. 2. The operational states 200 include at least a park state 210, a safety state 220 and an operational or walking state 230. The operational or walking state 230 further includes an automated mode 240 and a user-controlled mode 250.

The park state 210 indicates a state in which the exoskeleton system 100 of FIG. 1 is powered but the controller 110 will disregard any signals from sensors 170 and 180 of FIG. 2 for either automated or user-controlled movement of the lower extremities 20 and 30 of the user 10. In the park state 210, the controller 110 will not cause movement of the user's lower extremities 20 and 30. The park state 210 is an analogous state to an automobile with the engine running with automatic transmission in "park."

The safety state 220 indicates a state in which the exoskeleton system 100 of FIG. 1 is powered and the controller 110 is receiving user command signals from the sensors 170 and/or 180 indicative of an insecure gripping condition by the user 10 of at least one of the support handles 150. In the safety state 220, the controller 110 will inhibit certain movements or prohibit movement of the user's lower extremities 20 and 30. The insecure gripping condition may be indicated by, for example, less than a predetermined number of fingers of one hand being in secure contact with one of said support handles 150, or that a detected gripping pressure is below a predetermined or particular threshold pressure.

In contrast to the safety state 220, the operational or walking state 230 indicates a state in which the exoskeleton system 100 of FIG. 1 is powered and the controller 110 is receiving user command signals from the sensors 170 and 180 indicative of a secure gripping condition by the user 10 of at least one of the support handles 150. In the operational state 230, the controller 110 will cause the exoskeleton 100 to move lower extremities 20 and/or 30 of the user 10 in accordance with the selected automated mode 240 or user-controlled mode 250. In the automated mode 240, the controller 110 will cause the exoskeleton 100 to move the lower extremities 20 and 30 of the user 10 with a programmed gait having a predetermined stride length, HFC, speed and frequency.

If the user-controlled mode 250 is selected for the operational state 230, then the controller 110 will cause the exoskeleton 100 to move the respective lower extremities 20 and 30 of the user 10 in accordance with user command signals received from the sensors 170 and/or 180.

For example, a particular stride length producing a step by the user 10 is based on the application of hand grip pressure of greater than a particular pressure to at least one of the sensors 170 or 180 for a duration that would cause a corresponding duration of step movement by an associated leg support for one of the lower extremities. By alternating the pressure of the user 10 by her/his left and right hands on the support handles 150 will cause corresponding alternative movement of the lower extremities to cause a walking motion with stride lengths of the user's choosing. An exemplary method of operation for the user-controlled mode 250 of the operational state 230 is described in greater detail herein with regard to FIG. 4.

It should be readily understood that the state/mode selector sensor 190 is depicted on the support handle 150 in FIG. 2 for ease of explanation and that the such selector sensor may be omitted and its function accomplished by a sequence of finger contacts or gripping pressures applied to the sensor 170 or 180, or both in accordance with the present invention. For example, a state or mode change may be accomplished by the sensor 170, alone or in combination with the sensor 180, by the user 10 applying two deliberate quick squeezes of the support handle 150. Each deliberate squeeze being a rapid gripping pressure above a predetermined high level of gripping pressure of, for example, fifty percent (50%) of a user's maximal gripping pressure ("MGP"), for a short duration of, for example, on the order of approximately between 100 msec and 500 msec. Each deliberate squeeze being separated by a time of, for example, on the order of approximately between 100 msec and 500 msec with a gripping pressure of, for example, less than twenty percent (20%) of a user's MGP.

It should also be readily understood that the state or mode selection using the state/mode sensor switch 190 or otherwise would select either park state 210 or a walking/safety state 220/230 and that as described herein, the controller 110 would determine whether it is safe for the user 10 for the exoskeleton system 100 to cause movement of the user 10 or whether the exoskeleton system 100 should be in the safety state and inhibit all or certain movements of the user 10.

In addition, it is advantageous for the exoskeleton system 100 to include a feedback indicator (not shown) to alert the user 10 as to a selected state or mode or when the exoskeleton system 100 shifts between states and modes. Exemplary feedback indicators suitable for use with the exoskeleton system 100 include, for example, visual indicators such as light indicators (e.g., light emitting diodes ("LEDs") or liquid crystal displays ("LCDs")) disposed on the supports 140 or controller 110, audio indicators such as tones, sequence of beeps or tones, and voice indicators, and haptic indicators (e.g., vibrator devices included in the supports 140, controller 110 or elsewhere in the exoskeleton system 100).

Figure 4:
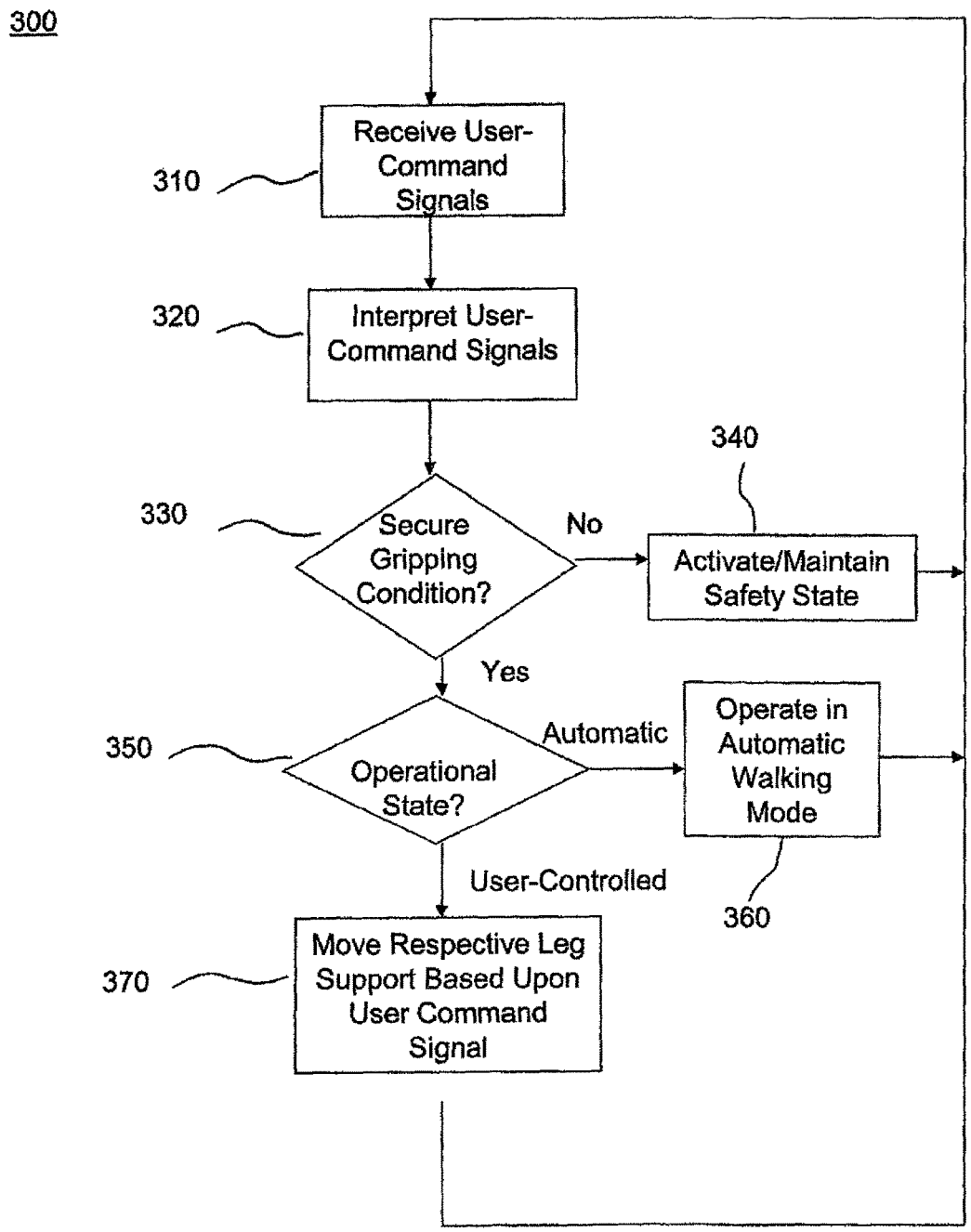
FIG. 4 is a flow diagram of a method for user-controlled gait in accordance with an exemplary embodiment of the present invention.

FIG. 4 depicts an exemplary method 300 performable by, for example, the controller 110 for causing the exoskeleton system 100 to move the user's respective lower extremities to produce a corresponding walking gait. The method 300 may be performed when the safety/operational state is selected by the user 10 using, for example, any one of the methods described above with regard to FIG. 3. The operations of the method 300 will now be described with reference to the exoskeleton system 100 and separate support device 140 of FIGS. 1 and 2.

Referring to FIG. 4, the method 300 begins with step 310 in which the controller 110 receives user command signals from the sensors 170 and 180 on the support handles 150. In step 320, the received user command signals in step 320 are interpreted or processed to determine if a secure gripping condition exists for at least one of the separate support devices 140. Then, in step 330, if an insecure gripping condition exists, the method 300 proceeds to step 340. In step 340, the safety state is activated for which the controller 110 inhibits all or certain movement of the user's lower extremities 20 and 30 that may be caused by the exoskeleton system 100. For example, in the safety state, the controller 110 may permit and cause certain limited movements of the exoskeleton and lower extremities 20 and 30 including, for example, turning left or right so that a lower extremity will avoid an obstacle, or to cause an advantageous or optimal separation distance between the user's lower extremities 20 and/or 30 before switching to the operational state. After entering or maintaining the safety state in step 340, the method 300 returns to step 310 to await receipt of further received user command signals.

Referring back to step 330, if a secure gripping condition is detected, then the method 300 proceeds to step 350. In step 350, the controller 110 determines if the user 10 selected the automated or user-controlled mode 240 or 250 for walking. If the automated mode 240 for walking is selected then the method 300 proceeds to step 360 and the controller 110 of the exoskeleton system 100 operates in automated walking mode wherein the controller 110 causes movement of the respective lower extremities with a programmed gait having, for example, a predetermined fixed stride length, frequency and speed, and HFC to produce a walking gait. These parameters will be predetermined based upon, for example, a user's height, weight, leg length and residual muscle function of the legs and torso.

The gait parameters of the automated mode 240 may be adjusted, for example, during initial programming of the exoskeleton system 100 for a particular user and/or after the exoskeleton system 100 is switched into the Park state 210. In the automated mode, the user 10 can start or stop the automated walking gait caused by the controller 110 by entering and exiting the safety state by adjusting gripping pressure on sensors 170 and 180. However, the user 10 is not able to control the stride length or speed of movement of each respective lower extremity in or near real-time. Once the exoskeleton system 100 is operated in automatic mode in step 360 the method 300 returns to step 310 to await further user command signals.

However, if in step 350, the controller 110 detects that the user 10 selected the user-controlled mode, the method 300 will proceed to step 370. In step 370, the controller 110 will then cause movement of a respective one of the user's lower extremities 20 or 30 starting at a time and for a duration based upon a corresponding starting time and duration that the user 10 applies a gripping pressure greater than a particular threshold on the support handle 150 as detected by the sensor(s) 170 and/or 180.

For example, when exoskeleton system 100 is in the user-controlled mode of the operational state, the user 10 may apply a gripping or squeezing pressure to the left support handle 150, which is greater than a particular threshold pressure to cause a desired movement of the right lower extremity 20 of the user 10. In accordance with this example, the controller 110, will cause movement of the actuator (not shown) and leg support 130 of the right-side lower extremity to effectuate a step by the user's right lower extremity 20 initiating and ending in accordance with start and duration that the user's gripping force is greater than the particular threshold pressure in the manner, for example, described in detail below with regard to FIG. 5.

After the movement of the lower extremity is completed in step 370 of FIG. 4, the method 300 returns to step 310 for the controller 110 to await further user commands from the sensor(s) 170 and/or 180. In following the above example, the user 10 would then apply a gripping pressure to the right support handle 150 above the particular threshold pressure to cause sequencing through the steps 310, 320, 330, 350, and 370 to produce a corresponding desired movement of the left lower extremity 20 of the user 10. In such manner, the user 10 can produce a user-controlled gait for walking and movement by alternatively provide gripping pressures to the right and left handle supports to cause alternative steps of desired stride length, speed and HFC, with the frequency of steps being controlled by the alternate application of gripping force to the respective right and left support handles 150. As is described in greater detail with regard to FIG. 5, the HFC may be adjusted or determined during each step by applying a predetermined or particular gripping pressure on the support handle 150 during a corresponding stride, or if the user wants to raise the foot higher for a particular stride to clear an obstacle, he/she can squeeze harder, i.e., apply greater gripping pressure, to achieve a greater HFC.

In an exemplary embodiment, suitable gripping threshold pressure to indicate a secure gripping condition in step 330 of FIG. 4 and exit the safety state 220 for indicating a user's desire for movement of the respective lower extremities may advantageously be above approximately ten percent (10%) of the user's MGP.

Figure 5:
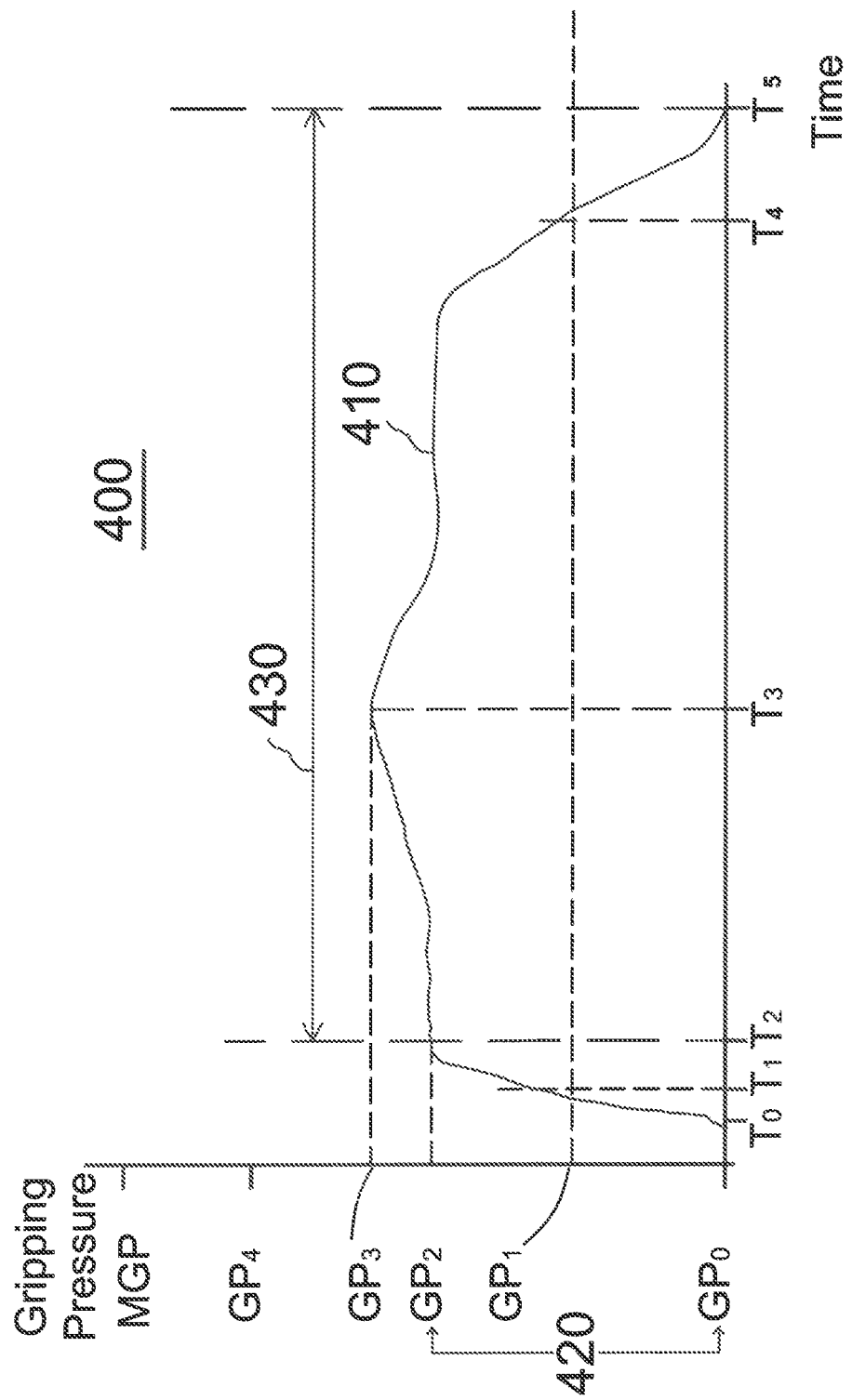
FIG. 5 is a graph depicting applied gripping pressure in accordance with the exemplary method of the present invention depicted in FIG. 4.

In accordance with the above described example to cause the exoskeleton system 100 to take a stride in the user-controlled mode in step 370, FIG. 5 depicts a graph 400 illustrating the manner in which a representative gripping force applied over time to the support handle 150 by the user 10 may advantageously control the start, speed, HFC and length of a stride produced by the exoskeleton system 100 in accordance with the above described example with regard to step 370 of FIG. 4. Referring to FIG. 5, in the graph 400, the y-axis depicts gripping pressure and the x-axis depicts time for the application of gripping pressure of the left support handle 150 to produce a corresponding step by the user's right lower extremity 20 (shown in FIG. 1). The maximum gripping pressure of the user 10 is denoted MGP on the y-axis. The maximum gripping pressure may be determined and set for the user 10 during the initial programming of the exoskeleton system 100 and/or after the exoskeleton system 100 is switched into the Park state 210 (shown in FIG. 3).

At the initiation of a step by controller 110, e.g., at time $T_0$, the user 10 begins increasing gripping pressure on the support handle 150 as shown by the increase in the gripping pressure curve 410 starting at $GP_0$ at such time $T_0$. At time $T_1$, the applied gripping pressure exceeds the gripping pressure $GP_1$ necessary to exit the safety state 210, such as, for example, on the order of ten percent (10%) of the user's MGP. Because the gripping force exceeds $GP_1$, the controller 110 measures the difference in the gripping force over a particular time period, e.g., 50 to 500 msec, from time $T_0$ to time $T_2$ to determine the speed or velocity at which the user's right lower extremity 20 should be moved. In FIG. 5, over the time period from time $T_0$ to time $T_2$ the difference in the gripping pressure is $GP_2$-$GP_0$ represented by the reference number 420. The larger the difference in the gripping pressure of $GP_2$-$GP_0$, the controller 110 will cause the user's right extremity 20 to move at a corresponding higher speed or velocity.

The gripping pressure applied by the user 10 after time $T_2$ is interpreted by the controller 110 to adjust the extent of the HFC, either relative to the ground or above the height of a preset HFC height. As a result, the HFC will be higher at time $T_3$ than at time $T_2$ because the gripping pressure curve 410 represents an application of greater pressure $GP_3$ at such time relative to the pressure $GP_2$ applied at time $T_2$. This control of the height of the foot enables the user 10 to step over objects or adjust to an uneven ground.

The corresponding stride duration implemented by the controller 110 is also based upon the gripping pressure detected by the sensors 170 and/or 180 on the support handle 150, by the user 10 decreasing the applied gripping pressure until the HFC is decreased to at or below the threshold gripping pressure $GP_0$ to inform the controller 110 to correspondingly decrease the height of the foot until it contacts the ground. In FIG. 5, the stride duration is the difference between times $T_5$ and $T_2$. The corresponding stride length for the step in this example would correspond to the controlled step velocity multiplied by this stride duration. Note, although the gripping force applied by the user 10 is reduced to lower the HFC to complete the step at time $T_5$, and correspondingly, the gripping pressure is reduced below $GP_I$ for entering the safety state at time $T_4$, the controller 110 is programmed to not enter the safety state until at least the step is complete at time $T_5$.

The gripping pressure $GP_4$ in FIG. 5 denotes an exemplary gripping pressure of, for example, fifty percent (50%) of a user's MGP, which may be useable with the double squeeze method described herein, for switching between modes or states in certain embodiments of the invention that do not incorporate or rely on the sensor 190 for mode/state switching.

The advantageous control of a gait of the exoskeleton system 100 by applied gripping pressure in above described embodiment depicted in FIG. 5 may be summarized as follows: (a) the frequency or steps for unit time, e.g., steps per minute is determined by rate of alternating the hand grip pressures applied to the right and left support handles 150; (b) the speed or velocity at which a lower extremity will move during a stride is determined by the increase in gripping pressure over a particular period of time, e.g., $T_0$ to $T_2$, at the start of a step; (c) The HFC during the stride is adjusted by the user 10 increasing or decreasing the gripping pressure during the stride; and (d) the user controls the stride length by adjusting gripping duration. A stride is ended when user 10 lowers her/his gripping pressure to $GP_0$ to result in lowering the HFC until the foot of the moving lower extremity contacts the ground.

The above example was described in which gripping force of the right-side support handle controlled the left-side lower extremity, and conversely, the gripping force of the left-side support handle controlled the right-side lower extremity was for illustration purposes only. Exoskeleton systems in accordance with the invention may also use a gripping force of the right-side support handle to control the right-side lower extremity, and a gripping force of the left-side support handle to control the left-side lower extremity.

Although the exemplary operation described with respect to the graph 400 in FIG. 5, the velocity of movement of a lower extremity is controlled by the difference in the gripping pressure $GP_2$-$GP_0$ over the time period from $T_0$ to $T_2$ as represented by the reference number 420. It should be understood that the velocity of movement of a lower extremity may alternatively be controlled by the duration it takes for the user to apply a gripping pressure that exceeds particular magnitude, such as for example, $GP_2$-$GP_0$. In such an embodiment example, the shorter the duration for the user to apply the gripping pressure $GP_2$-$GP_0$, the controller 110 will cause the user's lower extremity 20 to move at a corresponding higher velocity.

It should readily be understood by a person of ordinary skill in the art that in accordance with the invention, the advantageous use of gripping pressures may be applied to adjust the gait parameters of the stride start, stride speed, HFC, the stride length and step frequency may be upon a direct correspondence or used to alter default gait parameters. It should further be readily understood by a person of ordinary skill in the art that the use of machine learning algorithms, such as artificial neural networks or finite state automata algorithms, may additionally be used by the controller 110 so as to adjust default gait parameters during operation to adapt the system to a users preferred and comfortable gait parameters, such as, for example, the stride start, stride speed, HFC, the stride length and the stride frequency.

In an alternative embodiment of the present invention, when in the user-controlled mode of the operational state, varied rate of gripping pressure on a respective support handle may cause a corresponding change in speed or velocity of movement of the correspondingly controlled lower extremity, wherein the controller 110 causes an increase in velocity of the movement of the user's lower extremity based upon a corresponding increase in the rate of gripping pressure application onto at least one of the sensors 170 or 180 of the support handle 150. Further, the rate of alternating higher and lower gripping pressures, i.e., the number of such alternating gripping pressures applied in a unit of time (for example, a minute) determines the frequency of walking strides or number of strides over such unit of time.

The invention is further described by the following numbered paragraphs:

1. An exoskeleton system configured to be coupled to a user, comprising:
    first and second leg supports configured to be coupled to a user's lower limbs;
    first and second actuators respectively coupled to the first and second leg supports, said first and second actuators configured to provide movement of the exoskeleton;
    a controller coupled to said first and second actuators, said controller configured to shift said exoskeleton between a plurality of operational states including at least a safety state and an operational state based upon receipt of user command signals, and
    at least one support device separate from the exoskeleton to be held by a user of the exoskeleton for stabilization, said support device having at least one support handle, said support handle having at least one sensor coupled to the controller; said sensor for generating said user command signals based upon detecting an applied pressure, said controller for interpreting said user command signals to determine one of a secure gripping condition or an insecure gripping condition;
    wherein the controller causes the exoskeleton to operate in said safety state if said gripping condition is interpreted as insecure and said operational state if the gripping condition is interpreted as secure, and wherein in said operational state, said controller causes movement of the respective leg supports based upon receipt of user command signals indicative of said sensor detecting a predetermined contact or applied pressure.

2. The exoskeleton system of paragraph 1 wherein said insecure gripping condition is interpreted when said user command signals represent the applied pressure indicative that one hand is not in secure contact with one of said support devices.

3. The exoskeleton system of paragraph 1 wherein said safety state inhibits certain movement operations of one said lower limbs.

4. The exoskeleton system of paragraph 1 wherein when in said operational state, the controller causes the movement of a leg support for a particular stride length based on a duration of greater than a particular pressure to at least one sensor applied by the user to a first one of said support devices.

5. The exoskeleton system of paragraph 4 wherein when in said operational state the controller causes the movement of the other support for a particular stride length based on a duration of greater than said particular pressure to at least one sensor applied by the user to a second one of said support devices.

6. The exoskeleton system of paragraph 4 wherein when in said operational state the controller adjusts at least one gait parameter in accordance with varying gripping pressures applied by the user to a first one of said support devices.

7. The exoskeleton system of paragraph 6 wherein the controller adjust the gait parameter of speed of a leg support in accordance with speed of gripping pressure application and/or an increase in gripping pressure applied to at least one sensor of a first one of said support device by the user over a particular unit in time.

8. The exoskeleton system of paragraph 6 wherein the controller adjust the gait parameter of height of a foot of the user during a step based upon a gripping pressure applied to at least one sensor of a first one of said support device during said step.

9. The exoskeleton system of paragraph 6 wherein the controller adjust the gait parameter of stride duration of a step based upon a reduction in gripping pressure applied to at least one sensor of a first one of said support device by the user below a threshold pressure during said step.

10. The exoskeleton system of paragraph 1 wherein said at least one sensor comprise at least capacitive contact sensors.

11. The exoskeleton system of paragraph 1 wherein said at least one sensor comprise at least electro-mechanical switches.

12. The exoskeleton system of paragraph 1 wherein said support device is a crutch, cane or walker.

13. The exoskeleton system of paragraph 1 wherein said operational states include an automated mode and a self-control mode.

14. A method of operating an exoskeleton system, wherein said exoskeleton system comprises an exoskeleton having first and second supports configured to be coupled to a user's lower limbs, first and second actuators respectively coupled to the first and second supports, said first and second actuators configured to provide movement of the exoskeleton system; a controller coupled to said first and second actuators, at least one support device separate from the exoskeleton to be held by a user of the exoskeleton for stabilization, said support device having at least one support handle having sensors incorporated therein, the method comprising the steps of:

receiving by said controller user command signals generated by said sensors signals based upon detecting applied pressure;

interpreting by said controller said user command signals to determine one of a secure gripping condition or an insecure gripping condition, operating the exoskeleton in a safety state if said gripping condition is interpreted as insecure;

operating the exoskeleton in an operational state if the gripping condition is interpreted as secure; and when in said operational state, said controller causing movement of the respective supports based upon receipt of user command signals indicative of said sensor detecting a predetermined contact or applied pressure.

15. The method of paragraph 14 further comprising the step of interpreting said insecure gripping condition when said user command signals represent the applied pressure indicative that one hand is not in secure contact with one of said support devices.

16. The method of paragraph 14 further comprising the step of inhibiting certain movement operations of one said lower limbs when said exoskeleton is operated in said safety state.

17. The method of paragraph 14 further comprising the step of, when in said operational state, the controller causing movement of a leg support for a particular stride length based on a duration of greater than a particular pressure to at least one sensor applied by the user to a first one of said support devices.

18. The method of paragraph 17 further comprising the step of, when in said operational state, the controller causing the movement of the other support for a particular stride length based on a duration of greater than said particular pressure to at least one sensor applied by the user to a second one of said support devices.

19. The method of paragraph 14 further comprising the step of, when in said operational state, the controller adjusting at least one gait parameter in accordance with varying gripping pressures applied by the user to a first one of said support devices.

20. The method of paragraph 19 wherein said adjusting step further comprises adjusting the gait parameter of speed of a leg support in accordance with an increase in gripping pressure applied to at least one sensor of a first one of said support device by the user over a particular unit in time.

21. The method of paragraph 19 wherein said adjusting step further comprises adjusting the gait parameter of height of a foot of the user during a step based upon a gripping pressure applied to at least one sensor of a first one of said support device during said step.

22. The method of paragraph 19 wherein said adjusting step further comprises adjusting the gait parameter of stride duration of a step based upon a reduction in gripping pressure applied to at least one sensor of a first one of said support device by the user below a threshold pressure during said step.

23. A system useable with an exoskeleton configured to be coupled to a user, the system comprising:

a controller configured to be coupled to exoskelelton first and second actuators of repsective first and second supports configured to be coupled to a user's lower limbs, said controller configured to shift said exoskeleton between a plurality of operational states including at least a safety state and an operational state based upon receipt of user command signals; and at least one support device to be held by a user of the exoskeleton for stabilization, said support device having at least one support handle, said support handle having at least one sensor coupled to the controller; said sensor for generating user command signals based upon detecting an applied pressure, said controller for interpreting said user hand signals to determine one of a secure gripping condition or an insecure gripping condition;

wherein the controller is configured to cause the exoskeleton to operate in said safety state if said gripping condition is interpreted as insecure and said operational state if the gripping condition is interpreted as secure, and wherein in said operational state, said controller is configured to cause movement of the respective supports based upon receipt of user command signals indicative of said sensor detecting a predetermined contact or applied pressure.

It is to be understood that the invention is not limited to the particular embodiments of the invention described above, as variations of the particular embodiments may be made and still fall within the scope of the appended claims. Accordingly, this disclosure should be only limited by the scope of the claims attached hereto.

The invention claimed is:

1. An exoskeleton system configured to be coupled to a user, comprising:

first and second leg supports configured to be coupled to a user's lower limbs;

first and second actuators respectively coupled to the first and second leg supports, said first and second actuators configured to provide movement of the first and second leg supports;

a controller coupled to said first and second actuators, said controller configured to shift said exoskeleton system between a plurality of operational states including at least a safety state and an operational state based upon receipt of user command signals, and at least one support device separate from the exoskeleton system to be held by a user of the exoskeleton system for stabilization, said at least one support device having at least one support handle, said at least one support handle having at least one sensor coupled to the controller; said at least one sensor for generating said user command signals based upon detecting an applied contact pressure, said controller for interpreting said user command signals to determine one of a secure gripping condition or an insecure gripping condition;

wherein the controller is configured to cause the exoskeleton system to operate in said safety state if said gripping condition is interpreted as insecure and said operational state if a gripping condition is interpreted as secure, and wherein in said operational state, said controller is configured to cause movement of at least one of the leg supports with at least a gait parameter of speed of leg support adjusted in accordance with a rate of increase in gripping pressure applied to said at least one sensor by the user that is greater than a threshold gripping pressure over a particular period of time.

2. The exoskeleton system of claim 1 wherein said insecure gripping condition is interpreted when said user command signals represent the applied contact pressure indicative that one hand is not in secure contact with one of said at least one support devices.

3. The exoskeleton system of claim 1 wherein said safety state inhibits certain movement operations of one of said lower limbs.

4. The exoskeleton system of claim 1 wherein when in said operational state, the controller is configured to transmit signals to the first actuator to cause movement of the first leg support for a particular stride length based on a duration of time of continuous gripping pressure greater than the threshold gripping pressure to a first of the at least one sensor applied by the user to a first one of said at least one support devices.

5. The exoskeleton system of claim 4 wherein when in said operational state the controller is configured to transmit signals to the second actuator to cause movement of the second leg support for a particular stride length based on a duration of time of continuous gripping pressure greater than the threshold gripping pressure to a second of the at least one sensor applied by the user to a second one of said at least one support devices.

6. The exoskeleton system of claim 1 wherein the controller is configured to adjust the gait parameter of height of a foot of the user during a step based upon an increase of the gripping pressure applied to the at least one sensor-during said step.

7. The exoskeleton system of claim 1 wherein the controller is configured to adjust the gait parameter of stride duration of a step based upon a corresponding duration of maintaining the gripping pressure applied to the at least one sensor by the user above the threshold gripping pressure during said step.

8. The exoskeleton system of claim 1 wherein said at least one sensor comprises at least one capacitive contact sensor:

9. The exoskeleton system of claim 1 wherein said at least one sensor comprises at least one electro-mechanical switch.

10. The exoskeleton system of claim 1 wherein said at least one support device is a crutch, cane or walker.

11. The exoskeleton system of claim 1 wherein said operational states include an automated mode and a self-control mode.

12. A method of operating an exoskeleton system, wherein said exoskeleton system comprises first and second leg supports configured to be coupled to a user's lower limbs, first and second actuators respectively coupled to the first and second leg supports, said first and second actuators configured to provide movement of the first and second leg supports; a controller coupled to said first and second actuators, at least one support device separate from the exoskeleton to be held by a user of the exoskeleton system for stabilization, said at least one support device having at least one support handle having at least one sensor incorporated therein, the method comprising the steps of:

receiving by said controller user command signals generated by said at least one sensor based upon detecting an applied contact pressure;

interpreting by said controller said user command signals to determine one of a secure gripping condition or an insecure gripping condition, operating the exoskeleton system in a safety state if a gripping condition is interpreted as insecure;

operating the exoskeleton in an operational state if the gripping condition is interpreted as secure; and when in said operational state, said controller transmitting signals to said actuators to cause movement of at least one of the leg supports with at least a gait parameter of speed of leg support adjusted in accordance with a rate of increase in gripping pressure applied to said at least one sensor by the user that is greater than a threshold gripping pressure over a particular period of time.

13. The method of claim 12 further comprising the step of interpreting said insecure gripping condition when said user command signals represent the applied contact pressure indicative that one hand is not in secure contact with one of said at least one support device.

14. The method of claim 12 further comprising the step of inhibiting certain movement operations of one of said lower limbs when said exoskeleton is operated in said safety state.

15. The method of claim 12 further comprising the step of, when in said operational state, the controller transmitting signals to the first actuator to cause movement of the first leg support for a particular stride length based on a duration of time of continuous gripping pressure greater than the threshold gripping pressure to a first of the at least one sensor applied by the user to a first one of said at least one support device.

16. The method of claim 15 further comprising the step of, when in said operational state, the controller transmitting signals to the second actuator to cause movement of the second leg support for a particular stride length based on a duration of time of continuous gripping pressure greater than the threshold gripping pressure to a second of the at least one sensor applied by the user to a second one of said at least one support device.

17. The method of claim 12 wherein said adjusting step further comprises adjusting the gait parameter of height of a foot of the user during a step based upon an increase of the gripping-pressure applied to the at least one sensor during said step.

18. The method of claim 12 wherein said adjusting step further comprises adjusting the gait parameter of stride duration of a step based upon a corresponding duration of maintaining the gripping pressure applied to the at least one sensor by the user above the threshold gripping pressure during said step.

19. A system useable with an exoskeleton configured to be coupled to a user, the system comprising:
   a controller configured to be coupled to exoskeleton first and second actuators; said first and second actuators being coupled to first and second supports configured to be coupled to a user's lower limbs, said controller configured to shift said exoskeleton between a plurality of operational states including at least a safety state and. an operational state based upon receipt of user command signals; and
   at least one support device to he held by a user of the exoskeleton for stabilization, said at least one support device having at least one support handle, said at least one support handle having at least one sensor coupled to the controller; said at least one sensor for generating user command signals based upon detecting an applied pressure, said controller for interpreting said user command signals to determine one of a secure gripping condition or an insecure gripping condition;
   wherein the controller is configured to cause the exoskeleton to operate in said safety state if a gripping condition is interpreted as insecure and said operational state if the gripping condition is interpreted as secure, and wherein in said operational state, said controller is configured to cause movement of at least one of the leg supports with at least a gait parameter of speed of leg support adjusted in accordance with a rate of increase in gripping pressure applied to said at least one sensor by the user that is greater than a threshold gripping pressure over a particular Period of time.

* * * * *